(12) United States Patent
Kober et al.

(10) Patent No.: US 6,878,673 B2
(45) Date of Patent: Apr. 12, 2005

(54) AGENTS BASED ON A HOMOGENOUS PHASE, AND STABILIZATION THEREOF WITH AMMONIUM NITRATE AND USE OF SAID AGENTS AS BIOREGULATORS

(75) Inventors: Reiner Kober, Fussgönheim (DE); Wilhelm Rademacher, Limburgerhof (DE); Hans-Michael Fricke, Limburgerhof (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/433,427

(22) PCT Filed: Dec. 5, 2001

(86) PCT No.: PCT/EP01/14289

§ 371 (c)(1),
(2), (4) Date: Jun. 4, 2003

(87) PCT Pub. No.: WO02/45504

PCT Pub. Date: Jun. 13, 2002

(65) Prior Publication Data

US 2004/0031305 A1 Feb. 19, 2004

(30) Foreign Application Priority Data

Dec. 5, 2000 (DE) .......................................... 100 60 383

(51) Int. Cl.$^7$ ........................ A01N 33/12; A01N 43/40; A01N 43/84

(52) U.S. Cl. ........................ 504/130; 504/140; 504/144; 504/224; 504/248; 504/297; 504/345

(58) Field of Search ................................ 504/130, 140, 504/144, 224, 248, 297, 345

(56) References Cited

U.S. PATENT DOCUMENTS

| | | | |
|---|---|---|---|
| 3,542,538 A | 11/1970 | Jung | 71/76 |
| 3,905,798 A | 9/1975 | Zeeh et al. | 71/76 |
| 6,451,739 B1 | 9/2002 | Kober et al. | 504/224 |

FOREIGN PATENT DOCUMENTS

| | | |
|---|---|---|
| EP | 344533 | 12/1993 |
| GB | 944807 | 8/1960 |

*Primary Examiner*—S. Mark Clardy
(74) *Attorney, Agent, or Firm*—Novak Druce & Quigg, LLP

(57) ABSTRACT

The present invention relates to compositions based on a homogeneous, aqueous phase comprising at least one active ingredient from the class of the quaternized compounds, ethylene oxide/propylene oxide block copolymers and ammonium nitrate. Further active ingredients can be incorporated. The homogeneous phase is stabilized by ammonium nitrate. The use of the compositions as bioregulators is described.

20 Claims, No Drawings

AGENTS BASED ON A HOMOGENOUS PHASE, AND STABILIZATION THEREOF WITH AMMONIUM NITRATE AND USE OF SAID AGENTS AS BIOREGULATORS

The present invention relates to compositions based on a homogeneous, aqueous phase comprising at least one active ingredient from the class of the quaternized ammonium compounds, ethylene oxide/propylene oxide block copolymers and ammonium nitrate. Further active ingredients can be incorporated. The homogeneous phase is stabilized by ammonium nitrate. The use of the compositions as bioregulators is described.

With a view to industrial-scale production and the application of these active ingredients, the development of an effective composition is, besides the optimization of the active ingredient properties, of particular importance. An optimal balance between—in some cases contrary—properties such as biological activity, toxicology, possible effects on the environment and costs must be established by formulating the active ingredient(s) in an appropriate fashion. In addition, the formulation has a substantial effect on the shelf life of a composition and its user friendliness.

Some of the growth-regulatory active ingredients which are employed in the field of agriculture are quaternized compounds, whose most important representatives are N,N,N-trimethyl-N-β-chloroethylammonium chloride (CCC, chlorocholine chloride, chlormequat chloride, DE 12 94 734), N,N-dimethylmorpholinium chloride (DMC, DE 16 42 215) and N,N-dimethylpiperidinium chloride (DPC, MQC, mepiquat chloride, DE 22 07 575). These active ingredients, in particular chlormequat chloride and mepiquat chloride, are typically employed in cereal production at relatively high use concentrations. The application rate of these active ingredients per application is, as a rule, 0.3–1.5 kg/ha. The products are commercially available as aqueous active ingredient concentrates, as tablets or as granules (for example PIX®, Cycocel® DF and Terpal brands as SL mixtures, BASF Corporation).

These active ingredients from the class of the quaternized ammonium compounds can be employed together with further bioregulatory active compounds. For example, EP 0 344 533 describes synergistic combinations with growth-regulatory 3,5-dioxo-4-propionylcyclohexanecarboxylic acid derivatives such as prohexadione-calcium.

However, the need for as highly concentrated formulations as possible of this active ingredient from the class of the quaternized ammonium compounds can only be met to a certain extent, owing to its electrolyte character. As a rule, disadvantages result.

For example, highly concentrated, salt-like or electrolyte-comprising liquid formulations, for example the formulations described in U.S. Pat. No. 4,525,200, which is based on particular cationic and nonionic surfactants, can frequently not accommodate the desired amounts of activity-enhancing additives in sufficient quantities while remaining homogeneous. As a consequence, inhomogeneities, such as phase separations, and the possibility of application errors result.

On the other hand, the high hygroscopicity of the representatives of this class of active ingredients, in particular of chlormequat chloride and mepiquat chloride, do not permit inexpensive and highly concentrated formulations of solids which, in addition, would comprise large amounts of activity-enhancing additives. Such formulations are only possible in very limited form, for example in a water-soluble film bag, if at all.

As an alternative, EW or O/W (oil-in-water) formulations might be prepared. However, high amounts of electrolytes mean that rheological stabilization is a problem and can generally not be achieved by water-soluble sugar-based thickeners, for example xanthan gum or cellulose derivatives. The result is creaming, which can lead to erroneous applications.

This problem complex is solved according to WO 00/07445 insafar as the use of specific auxiliaries, in particular alkyl glucosides and long-chain cationic surfactants, leads to substantially homogeneous SL formulations. It emerges that the mixtures of N,N,N-trimethyl-N-β-chloroethylammonium chloride and PO/EO block copolymers in water, which are biphasic per se. can be converted into homogeneous to weakly-turbid mixtures by addition of 2-ethylhexyl glucoside or ricinoleic acid propylamidotrimethylammonium methosulfate. However, the amount of PO/EO block polymers which can be accommodated while retaining homogeneity is limited in a disadvantageous fashion.

It is an object of the present invention to provide stable liquid formulations based on an aqueous, homogeneous phase with sufficient amounts of at least one active ingredient from the class of the quaternized ammonium compounds and ethylene oxide/propylene oxide block copolymers. We have found that this object is achieved by the addition of ammonium nitrate.

The present invention therefore relates to compositions based on a homogeneous phase, comprising
(a) at least one active ingredient of the formula (I)

where $R^1$, $R^2$ and X have the following meanings:
$R^1$ is alkyl;
$R^2$ is alkyl, cyclopentenyl, haloalkyl; or $R^1$ and $R^2$ together are a radical —$(CH_2)_5$—, —$(CH_2)_2$—O—$(CH_2)_2$— or —$(CH_2)$—CH=CH—$(CH_2)$—NH—;
X is an anionic group;
(b) water,
(c) at least one optionally end-capped ethylene oxide/propylene oxide block copolymer;
(d) ammonium nitrate.

As a rule, the homogeneous phase according to the invention is fluid, in particular liquid. Homogeneous means, in accordance with the invention, especially a uniform distribution of the active ingredient content in the phase. In this sense, the property of homogeneity, which is desirable in accordance with the invention, is achieved when erroneous applications owing to inhomogeneities are not to be expected upon use in practice. Thus, in particular cases, the homogeneous phase may also encompass a plurality of phases as long as they are sufficiently finely distributed within each other. In particular, microphasic mixtures must be mentioned in this context. The appearance of the homogeneous phase is preferably clear or transparent, but it may also be opaque, weakly turbid, slightly turbid or turbid. Turbidities may be the result of, for example, microparticulate auxiliaries, for examples silicones or mineral constituents. Also, the viscosities of the phase can vary within a wide range. Preferably, homogeneous phases according to the invention are sparingly viscous, viscous or highly viscous. It is particularly advantageous when the homogeneous phase is flowable. According to this aspect, the apparent viscosities, which can be determined following OECD guideline 114 using a Viscolab LC 10 apparatus by Physica or a Rheomat 115 are in a range of from approximately 5 mPas to 2 000 mPas. preferably from approximately 10 mPas to 500 mPas and in particular from approximately 20 mPas to 300 mPas.

In accordance with a further aspect, the homogeneous phase according to the invention has a density of at least 1.04 g/l and preferably of at least 1.07 g/l. The maximum density of fluid and in particular liquid homogeneous phases results from the transition into the solid state.

In accordance with a particular embodiment, the state of the homogeneous phase according to the invention is gel-like.

The homogeneous phase encompasses at least 4 components (a), (b), (c) and (d). Such a 4-component system is preferably 1-phase in accordance with the invention.

Compositions according to the invention are based on such a 4-component system and can therefore also be 1-phase. In addition, the compositions may comprise further components, for example components (e), (f) and (g) according to the invention. In this context, the further components can be distributed in the homogeneous phase in principle in any form, for example they can be dissolved, dispersed or suspended therein. In specific cases, this may result in the formation of one or more further phases, so that such cases also encompass multiphase, in particular 2- and 3-phase, compositions.

Compositions according to the invention belong to the group of the liquid formulations. These include, in particular, water-soluble concentrates (SL formulations), suspension concentrates (SC formulations), suspoemulsions (SE formulations) and microemulsions.

In accordance with a preferred embodiment, water-soluble concentrates (SL formulations) are provided. They are based on a homogeneous phase according to the invention which, being the fluid or liquid phase, comprises possible further components in dissolved form.

In accordance with a further special embodiment of the present invention, suspension concentrates (SC) are provided. Such suspension concentrates are based on a homogeneous phase according to the invention, which, being the fluid or liquid phase, is mixed with a solid phase. The solid is advantageously present in dispersed form. The formation of stable dispersions is preferred.

As a rule, a solid active ingredient is present in particulate form. The mean particle size of the active ingredient particles is advantageously less than 10 μm and in particular less than 5 μm. Advantageous particle sizes are within a range of from 0.1 μm to 10 μm and in particular from 0.5 μm to 5 μm. In accordance with a further aspect, advantageous cumulative frequency distributions of particle sizes can be described by at least 50% of the particles having a particle size of less than 100 μm, preferably of less than 50 μm and in particular of less than 10 μm. Suspension concentrates with cumulative frequency distributions of particle sizes according to which at least 90% of the active ingredient particles have a particle size of less than 10 μm and in particular less than 5 μm are especially preferred. The above statements on particle sizes refer to measurements at room temperature using the Cilas granulometer 715 of Cilas, Marcoussis, France, which measures solid-saturated samples which, if required, are diluted with the fluid homogeneous phase of the SC according to the invention.

The compositions according to the invention exhibit outstanding stabilities, which offer in particular good user friendliness. Thus, the compositions according to the invention should, under the use conditions, essentially retain a particular state at least over the application period of, as a rule, a few hours. It is particularly advantageous when the phase of the compositions which encompasses components (a) to (d) is homogeneous at least for a duration of 5, preferably 8 and in particular 12 hours. Under the aspect of stability, compositions which are particularly preferred are those where no noticeable phase separation of the homogeneous phase according to the invention is observed in the course of 2 weeks' storage at 54° C. (CIBAC 1-MT46,1.3). 1 week's storage at 0° C. (CIPAC 1-MT39), and/or 2 months' storage at 45° C., or where under certain circumstances, for example at a temperature higher than the test temperatures, phase separations occur, but the compositions can be rehomogenized by cooling and, if appropriate, expedient moving (reversible phase separation). According to this aspect, homogeneous phases with opaque, weakly turbid, slightly turbid or turbid appearance which are preferred are those which show these stabilities.

Based on the total weight of the composition, the homogeneous phase can amount to 100% by weight. In the case of suspension concentrates, it generally amounts to 10 to 99% by weight, preferably 30 to 95% by weight and in particular 40 to 80% by weight.

Special active ingredients of the formula (I) result when alkyl is methyl, ethyl, isopropyl. Preferred as the haloalkyl group is the 2-chloroethyl group. If the substituents together with the nitrogen atom to which they are bonded form a cyclic radical, $R^1$ and $R^2$ are preferably a morpholino or piperidino group, X is, for example, a halide such as bromide and preferably chloride; sulfate; alkyl sulfate, such as methyl sulfate; alkylsulfonate, such as methylsulfonate; or another agriculturally useful anionic group. In principle, divalent anionic groups are also suitable, and these are employed in the stoichiometric amounts which correspond to the ammonium cation.

The active ingredient of the formula I is preferably selected from among (a1) N,N,N-trimethyl-N-β-chloroethylammonium chloride (CCC), of the formula (Ia).

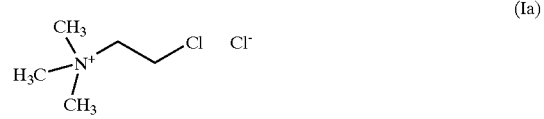

(a2) N,N-dimethylpiperidinium chloride (MQC), of the formula (Ib).

and (a3) N,N-dimethylmorpholinium chloride (DMC), of the formula (Ic)

(Ic)

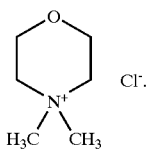

Especially preferred are the active ingredient components (a1) and/or (a2).

In accordance with an embodiment of the present invention, active ingredient component (a) essentially consists of a compound of the formula (Ia) or (Ib) or a mixture of these.

In particular, the present invention relates to compositions with high amounts of active ingredient (concentrates). Thus, component (a) generally amounts to more than 10% by weight, preferably to more than 20% by weight and in particular to more than 25% by weight of the total weight of the composition. On the other hand, as a rule, component (a) expediently amounts to less than 70% by weight, preferably to less than 60% by weight and in particular to less than 50% by weight of the total weight of the composition.

Unless otherwise specified, quantities in the present description are generally intended to refer to the total weight of the composition. As a rule, the term "essentially" refers, in accordance with the invention, to a percentage ratio of at least 90%, preferably of at least 95% and in particular at least 98%.

The compositions according to the invention comprise water. The water acts in particular as a solvent for the active ingredient component (a). In addition, high amounts of water favor the homogeneity and flowability of mixtures of active ingredient component (a) and EO/PO block copolymers. As a rule, it is expedient for the water to amount to more than 10% by weight, preferably to more than 20% by weight and in particular to more than 25% by weight of the total weight of the composition. On the other hand, high amounts of water can adversely affect the stability of the compositions in particular when further active ingredients which are sensitive to hydrolysis, for example in the form of a solid phase, are introduced into the homogeneous phase, as is the case for example with SC formulations. Also, high amounts of water may have an adverse effect on the sedimentation of solid components, owing to the reduced viscosity. According to these aspects, it is advantageous for the water to amount to less than 60% by weight, preferably to less than 55% by weight and in particular to less than 45% by weight of the total weight of th composition.

The ethylene oxide/propylene oxide block copolymers or their end-capped derivatives, which are to be used, in accordance with the invention, as component (c), are known per se; cf., for example, Fiedler H. P. Lexikon der Hilfsstoffe für Pharmazie, Kosmetik und angrenzende Gebiete [Dictionary of Adjuvants for Pharmacy, Cosmetics and Related Fields], Editio Cantor Verlag Aulendorf, 4th edition, 1996, entries "Pluronics", "poloxamer". These are nonionic surfactants used widely in pharmacy, cosmetics, crop protection and related fields.

Preferred in accordance with the invention are the optionally end-capped ethylene oxide/propylene oxide block copolymers selected from among polymers of the formula (IVa)

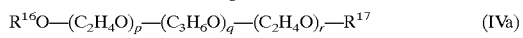  (IVa)

or polymers of the formula (IVb)

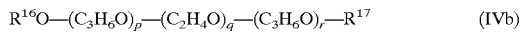  (IVb)

where p, q, r independently of one another correspond to a value in the range of from 2 to 300, preferably from 5 to 200 and in particular from 10 to 150 and $R^{16}$, $R^{17}$ independently of one another are hydrogen or $C_1$–$C_4$-alkyl, $C_1$–$C_4$-alkyl-CO, in particular methyl, t-butyl and acetyl, and further groups which are suitable for end-capping.

Compared with the block copolymers of the formula (IVa), the block copolymers of the formula (IVb) are also referred to as inverse block copolymers.

Preferably, the weight-average molecular weight of block copolymers to be used in accordance with the invention is at least 500, preferably at least 1 000 and in particular at least 2 000. As a rule, block copolymers are used whose weight-average molecular weight is less than 50 000, preferably less than 25 000 and in particular less than 15 000. Preferred ranges of weight-average molecular weights are 500 to 15 000, preferably 1 000 to 15 000, in particular 2 000 to 10 000.

The block copolymers of this type which are used in practice generally constitute mixtures of various polymer chains whose molecular weight and, in particular, EO/PO distribution varies within certain limits, p, q and r therefore indicate the mean degree of alkoxylation of the molecule segment in question.

The surface-active properties of the EO/PO block copolymers depend on the size and arrangement of the EO or PO blocks. As a rule, the EO block(s) form the hydrophilic moiety of the molecule, while the PO block(s) form the hydrophobic moiety of the molecule.

In EO/PO block copolymers of the formula (IVa), the EO percentage based on the total weight of the block copolymer is, as a rule, 10 to 80% by weight, higher molecular weights being preferred with increasing EO percentages.

In inverse EO/PO block copolymers of the formula (IVb), the EO percentage based on the total weight of the block copolymer is preferably more than 10% by weight and in particular more than 20% by weight.

EO/PO block polymers can be prepared in a manner known per se by subjecting ethylene oxide to an addition reaction with propylene glycols and/or propylene oxide to an addition reaction with ethylene glycols. Accordingly, agreement generally results for the values of p and r, which is due to the preparation.

In addition, a large number of representatives of such block copolymers and inverse block copolymers are commercially available, EO/PO block copolymers which must be mentioned by way of example in this context are those of the formula (IVa), which are available from BASF under the tradename Pluronic, in particular the embodiments L 121 with 10% by weight of EO and a weight-average molecular weight of 4 400 and p+r=10; q=68; 10 R 5 with 50% by weight of EO and a weight-average molecular weight of 1 950 and p+r=22; q=17; 17 R 5 with 40% by weight of EO and a weight-average molecular weight of 2 650 and p+r=24; q=27; 25 R 4 with 40% by weight of EO and a weight-average molecular weight of 3 600 and p+r=33; q=37; PE 6400 with 40% by weight of EO and a weight-average molecular weight of 2 900 and p+r=26; q=30; PE 6800 with 80% by weight of EO and a weight-average molecular weight of 8 000 and p+r=145; q=28; PE 10500 with 50% by weight of EO and a weight-average molecular weight of 6 500 and p+r=74; q=56, EO/PO block copolymers are also known under the CTFA name poloxamer. Poloxamers which can be used in accordance with the invention are mentioned, for example, in H. P. Fiedler: Lexikon der Hilfsstoffe für Pharmazie, Kosmetik und angrenzende Gebiete; Editio Cantor Verlag, Aulendorf, 4th revised and enlarged edition (1996), 1203. Others to be mentioned are the EO/PO block copolymers which are available from Uniqema/ICI under the tradename Synperonics, in particular the PE F, PE L and PE P types, and those available from Clariant under the tradename Genapol, in particular Genapol PF 20, 80 and 10 with 20, 80 and 10% by weight of EO, respectively. The inverse EO/PO block copolymers of the formula (IVb) available from BASF under the tradename Pluronic may furthermore be mentioned.

As a rule, end-capped EO/PO block copolymers are based on the above-described block copolymers. In such end-capped block copolymers, the terminal hydroxyl groups are reacted with suitable groups, preferably etherified or esterified with $C_1$–$C_4$-alkyl or -alkoyl groups, in particular methyl, t-butyl and acetyl groups.

The EO/PO block copolymers of the formula (IVa) are preferred.

The EO/PO block copolymers have adjuvant, in particular activity-enhancing, properties. Thus, the addition of such additives as wetters makes possible an accelerated uptake of active ingredients by the plant. Amounts of component (c) of more than 5% by weight, preferably of more than 7.5% by weight, and in particular of more than 10% by weight of the total weight of the composition are advantageous. On the other hand, amounts of components (c) of less than 50%, preferably of less than 35% and in particular of less than 30% by weight of the total weight of the composition are expedient, as a rule.

A characteristic of compositions according to the invention is, in particular, that the homogeneous phase comprises ammonium nitrate as component (d). Surprisingly, the addition of ammonium nitrate allows the formulation of a homogeneous mixture of components (a), (b) and (c) according to the invention. It is especially advantageous that this can be done successfully even when the water content is relatively low.

The present invention therefore also relates to the use of ammonium nitrate for homogenizing a mixture encompassing (a) at least one active ingredient of the formula (I)
(b) water;
(c) at least one optionally end-capped ethylene oxide/propylene oxide block copolymer.

This homogenization relates in particular to the conversion of heterogeneous, in particular 2-phase mixtures, into homogeneous, in particular 1-phase, mixtures of said composition. The addition of ammonium nitrate contributes to th stabilization of the homogeneous phase according to the invention. In particular, the use of ammonium nitrate permits a rheological stabilization of mixtures of components (a), (b) and (c) according to the invention. Thus, the viscosity can be modulated in the desired fashion. The density is increased, which counteracts in particular sedimentation of a solid phase and is therefore of particular advantage in the case of SC formulations. Moreover, the combination according to the invention, of component (c) and (d), makes possible a formulation from which ammonium salts, in particular ammonium chloride, essentially do not precipitate even when the water contents are relatively low. Furthermore, the use of ammonium nitrate has a positive effect, in particular an activity-enhancing effect, on the biological activity of the bioregulators formulated in accordance with the invention.

As a rule, component (d) amounts to from 5 to 40% by weight, preferably from 10 to 35% by weight and in particular from 15 to 30% by weight of the total weight of the composition.

In accordance with a particular embodiment of the present invention, the compositions comprise at least one further bioregulator as component (e).

Useful bioregulators include, for example, 3,5-dioxo-4-propionylcyclohexanecarboxylic acid derivatives, for example those described in EP 0 598 404 A1.

In accordance with a preferred embodiment, compositions according to the invention comprise (e1) at least one active ingredient of the formula (II)

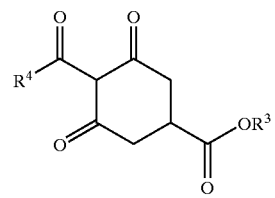

(II)

where $R^3$ and $R^4$ have the following meanings:
$R^3$ is hydrogen, alkyl, alkyl-S-alkyl, phenyl, substituted phenyl, the substituents preferably being selected from among alkyl, halogen and alkoxy;
$R^4$ is alkyl, cycloalkyl, benzyl, substituted benzyl, phenethyl, phenoxymethyl, 2-thienylmethyl, alkoxymethyl, alkylthiomethyl, the substituents preferably being selected from among alkyl, halogen and alkoxy;
or an agriculturally useful salt thereof.

Preferably, the radical $R^4$ represents ethyl and the radical $R^3$ represents hydrogen, alkyl or an agriculturally useful cation, for example an alkali metal ion, alkaline earth metal ion, mono-, di- or trialkylammonium or the like.

It must be noted that the representation referred to as formula (II) also encompasses isomeric, in particular tautomeric, forms of the structure shown. This is illustrated for example with reference to formula (IIa).

Especially preferred are the active ingredients defined in tables 1 to 4 of EP 0 598 404 A1, which active ingredients are part of the present description. Very especially preferred as active ingredient of the formula (II) is a prohexadione salt, in particular the calcium salt, of the formula (IIa)

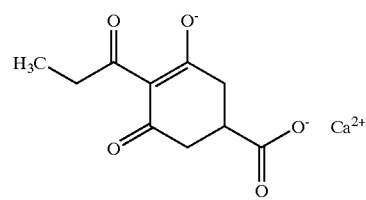

(IIa)

As a rule, component (e1)—if present—amounts to from 0.5 to 30% by weight, preferably from 2 to 25% by weight and in particular from 4 to 20% by weight of the total weight of the composition.

Preferably, the total amount of component (e1) present in the composition is at least partially present as a solid. Another amount, as a rule less, can be dissolved in the homogeneous phase. The dissolved component (e1) advantageously amounts to less than 1% by weight, preferably to less than 0.5% by weight and in particular to less than 0.3% by weight of the total amount present in the composition.

Other examples of bioregulators which are useful as component (e2) are gibberellins, in particular active ingredients of the formula (IIIa)

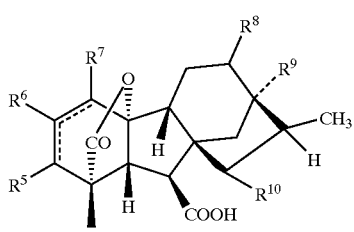

(IIIa)

where the radicals $R^5$, $R^6$, $R^7$, $R^8$, $R^9$ and $R^{10}$ independently of one another are hydrogen or hydroxyl and the broken line denotes an optional double bond either between the carbon atoms in positions 1 and 2 or between the carbon atoms in positions 2 and 3;
and active ingredients of the formula (IIIb)

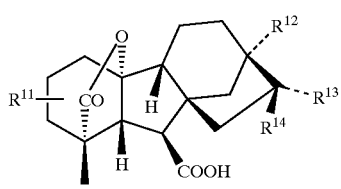

(IIIb)

where $R^{11}$ indicates that ring A (i) has no further functionality, or (ii) has a 1,2-double bond or a 2,3-double bond or (iii) has OH, F, Cl or Br in position 3α or 3β, it being possible for a 1,2-double bond to be present or not, or (iv) has OH, F, Cl or Br in position 1α or 1β, it being possible for a 2,3-double bond to be present or not;
$R^{12}$ is H or OH, OC(=O)$R^{15}$ or O$R^{15}$;
$R^{13}$, $R^{14}$ independently of one another are H, F, Cl, Br, alkyl, alkenyl, cycloalkyl or $CH_2X$, where X is F, Cl or Br;
$R^{15}$ is alkyl.

Such 16,17-dihydrogibberellins and further gibberellins which are useful in accordance with the invention are mentioned, for example, in WO 93/03616, WO 96/06090 and in particular in WO 00/02454. Particular compounds of the formula (IIIa) are defined in WO 00/02454 on pages 4 and 5 as compounds of the formulae (II) to (IX). These gibberellins are also part of the present description.

Particularly preferred is the active ingredient exo-16,17-dihydro-GA5-13-acetate, of the formula (IIIc)

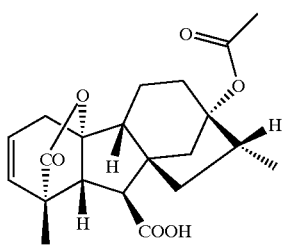

(IIIc)

As a rule, component (e2)—if present—amounts to from 0.1 to 5% by weight, preferably from 0.2 to 3% by weight and in particular from 0.25 to 1.5% by weight of the total weight of the composition.

As a rule, the total amount of component (e2) present in the composition is at least partially dissolved in the homogeneous phase. Another amount, as a rule less, can be present as a solid in the homogeneous phase.

In accordance with a particular embodiment of the present invention, the compositions encompass not only active ingredient component (a), but also active ingredient component (e1), that is to say in particular chlormequat chloride and/or mepiquat chloride of the formulae (Ia) and (Ib), respectively, together with prohexadione-calcium, of the formula (IIa). Thus, this embodiment relates to compositions based on a bioregulatory active ingredient combination (combination product). This bioregulatory active ingredient combination can be complemented in particular by an active ingredient component (e2).

The relative amounts of active ingredient in combination products are largely variable. According to one aspect, the compositions contain relatively greater amounts by weight of active ingredient component (a) than of active ingredient component (e1). This weight ratio of (a) to (e1) is typically in a range of from 1.5:1 to 20:1, preferably from 2:1 to 20:1 and in particular from 2.5:1 to 10:1.

In accordance with a particular embodiment of the present invention, the compositions comprise at least one further surfactant as surface-active component (f). In the present context, the term "surfactant" refers to agents which lower the interfacial tension or to surface-active agents.

Component (f) serves similar purposes as component (c). In particular, (f) is added as dispersant or emulsifier, especially for dispersing a solid component in suspension concentrates. Furthermore, component (f) may act in part as wetter.

Surfactants which can be used in principle are anionic, cationic and amphoteric surfactants, polymer surfactants and surfactants with hetero atoms in the hydrophobic group being included.

The anionic surfactants include, for example, carboxylates, in particular alkali metal salts, alkaline earth metal salts and ammonium salts of fatty acids, for example potassium stearate, which are conventionally also termed soaps; acyl glutamates; sarcosinates, for example sodium lauroyl sarcosinate; taurates; methylcelluloses; alkyl phosphates, in particular alkyl monophosphoric esters and alkyl diphosphoric esters; sulfates, in particular alkyl sulfates and alkyl ether sulfates; sulfonates, further alkylsulfonates and alkylaryl sulfonates, in particular alkali metal salts, alkaline earth metal salts and ammonium salts of arylsulfonic acids and of alkyl-substituted arylsulfonic acids, of alkybenzenesulfonic acids such as, for example, lignosulfonic acid and phenylsulfonic acid, of naphthalene- and dibutylnaphthalenesulfonic acids, or dodecylbenzenesulfonates, alkylnaphthalenesulfonates, alkyl methyl ester sulfonates, condensates of sulfonated naphthalene and derivatives thereof with formalehyde, condensates of naphthalenesulfonic acids, phenol- and/or phenolsulfonic acids with formaldehyde or with formaldehyde and urea, mono- or dialkylsulfosuccinates; and protein hydrolysates and ligno-sulfite waste liquors. The abovementioned sulfonic acids are advantageously used in the form of their neutral or, if appropriate, basic salts.

The cationic surfactants include, for example, quaternized ammonium compounds, in particular alkyltrimethylammonium halides, alkyltrimethylammonium alkylsulfates, dialkyldimethylammonium halides and dialkyldimethylammonium alkylsulfates, and pyridine and imidazoline derivatives, in particular alkylpyridinium halides.

The nonionic surfactants include, for example, the compounds of the formula (V), further alkoxylates and especially ethoxylates, and nonionic surfactants, in particular fatty alcohol polyoxyethylene esters, for example lauryl alcohol polyoxyethylene ether acetate, alkyl polyoxyethylene ethers and alkyl polyoxypropylene ethers, for example of isotridecyl alcohol, and fatty alcohol polyoxyethylene ethers, alkylaryl alcohol polyoxyethylene ethers, for example octylphenol polyoxyethylene ether, alkoxylated animal and/or vegetable fats and/or oils, for example corn oil ethoxylates, castor oil ethoxylates, tallow fat ethoxylates, glycerol esters, such as, for example, glycerol monostearate, fatty alcohol alkoxylates and oxoalcohol alkoxylates, in particular of the type RO—$(R_{19}O)_x(R_{20}O)_yR_{21}$ where $R_{19}$ and $R_{20}$ independently of one another=$C_2H_4$, $C_3H_6$, $C_4H_8$ and $R_{21}$=H, or $C_1$–$C_{12}$-alkyl, R=$C_3$–$C_{30}$-alkyl or $C_6$–$C_{30}$-alkenyl, x and y independently of one another being 0 to 50, it not being possible for both to be 0, such as isotridecyl alcohol and oleyl alcohol polyoxyethylene ether, alkylphenol alkoxylates, such as, for example, ethoxylated isooctyl-, octyl- or nonylphenol, tributylphenol polyoxyethylene ether, fatty amine alkoxylates, fatty acid amide alkoxylates and fatty acid diethanolamide alkoxylates, in particular their ethoxylates, sugar surfactants, sorbitol esters such as, for example, sorbitan fatty acid esters (sorbitan monooleate, sorbitan tristearate), polyoxyethylene sorbitan fatty acid esters, alkylpolyglycosides, N-alkylgluconamides, alkyl methyl sulfoxides, alkyldimethylphosphine oxides, such as, for example, tetradecyldimethylphosphine oxide.

The amphoteric surfactants include, for example, sulfobetaines, carboxybetaines and alkyldimethylamine oxides, for example tetradecyldimethylamine oxide.

The polymeric surfactants include, for example, di-, tri- and multiblock polymers of the type $(AB)_x$, ABA and BAB, for example polystyrene block polyethylene oxide, and AB comb polymers, for example polymethacrylate comb polyethylene oxide.

Further surfactants to be mentioned here by way of example are perfluoro surfactants, silicone surfactants, phospholipids such as, for example, lecithin or chemically modified lecithins, amino acid surfactants, for example N-lauroylglutamate, and surface-active homo- and copolymers, for example polyvinylpyrrolidone, polyacrylic acids in the form of their salts, polyvinyl alcohol, polypropylene oxide, polyethylene oxide, maleic anhydride/isobutene copolymers and vinylpyrrolidone/vinyl acetate copolymers.

Unless otherwise specified, the alkyl chains of the above-mentioned surfactants are linear or branched radicals having usually 8 to 20 carbon atoms.

The further surfactant for component (f) is preferably selected from among nonionic surfactants. Preferred among these are (f1) nonionic surfactants of the formula (V),

where $R^{18}$ is a straight-chain or branched, saturated or unsaturated, unhydroxylated, monohydroxylated or dihydroxylated aliphatic radical having 8 to 30 carbon atoms, the total of all x is zero to 100, y is 1 to 7, $A^1$ is hydroxyl or alkoxy if y is 1 or $A^1$ is derived from a polyol if y is 2 to 7.

These are optionally ethoxylated carboxylic acids and esters of mono- or polyfunctional alcohols (polyols).

The radical $R^{18}$ is derived in particular from fatty acid residues, for example those mentioned above, so that $R^{18}$ is expediently a straight-chain or branched, in particular singly to doubly-branched, saturated or unsaturated, in particular mono-, di- or triunsaturated, optionally mono- or dihydroxylated aliphatic radical having 8 to 30, preferably 12 to 24 and in particular 10 to 24 carbon atoms. These include, in particular, palmityl, stearyl, arachidyl, hexadecenyl, oleyl, linolyl, linolenyl, ricinoleyl, eicosanyl and mono- and dihydroxystearyl, of which ricinoleyl and oleyl are preferred.

If the nonionic surfactants of the formula (V) are ethoxylated, the total of all x gives the mean ethoxylation number as, as a rule, 3 to 100 and in particular 5 to 50.

If $A^1$ is hydroxyl, y=1 and the mean ethoxylation number is advantageously 5 to 50 and preferably 15 to 40. Suitable polyethoxylates which must be mentioned in this context are, in particular, castor oil polyethoxylates and oleic acid polyethoxylates.

If $A^1$ is optionally branched alkyloxy having 1 to 4, preferably 1 or 2, carbon atoms, y=1 and the mean ethoxylation number is 3 to 100 and preferably 20 to 50.

If $A^1$ is derived from a polyol having 3 to 7 and in particular 6 carbon atoms, the value of y=2 to 7 and preferably 3 to 6. Here, y hydroxy hydrogen atoms of the radical $A^1$ are replaced by in each case one radical $R^{18}$—CO-$(EO)_x$-, it being possible for two or more radicals $R^{18}$ and two or more indices x to be identical or different. Preferably, two or more radicals $R^{18}$ are identical, while the indices x may be different and, as a rule, follow a normal distribution. In particular, $A^1$ is derived from a sugar alcohol, such as sorbitol or glycerol. A preferred meaning of $A^1$ is sorbitol. If ethoxylated, the mean ethoxylation number is 5 to 50 and preferably 15 to 40. Substances which must be mentioned in this context are, in particular, the corresponding sorbitol polyethoxyoleates and sorbitol poly(iso) stearates.

Very especially preferred as component (f1) are castor oil polyethoxylates, sorbitol polyethoxyoleates and mixtures of these.

As a rule, component (f), in particular component (f1),—if present—amounts to from 0.5 to 30% by weight, preferably from 1 to 25% by weight and in particular from 5 to 15% by weight of the total weight of the composition.

In accordance with a particular embodiment of the present invention, the compositions comprise at least one further auxiliary as component (g).

Component (g) can have a multiplicity of purposes. Suitable auxiliaries are selected by the skilled worker by generally customary methods to suit the demands.

For example, further auxiliaries are selected from among (g1) calcium salts;

(g2) chelating agents;

(g3) urea;

(g4) further solvents or diluents.

The calcium salts include salts of inorganic and organic acids, in particular hydroxides, nitrates and halides of inorganic acids, or carbonates and sulfonates of organic carboxylic acids and sulfonic acids. Preferably, the calcium salts are soluble in the homogeneous phase.

As a rule, component (g1), if present, amounts to from 0.1 to 7.5% by weight, preferably from 0.2 to 5% by weight and in particular from 0.4 to 3% by weight of the total weight of the composition.

Preferred chelating agents are compounds which form complexes with heavy metals and in particular with transition metals, for example EDTA and its derivatives.

As a rule, component (g2), if present, amounts to from 0.001 to 0.5% by weight, preferably from 0.005 to 0.2% by weight and in particular from 0.01 to 0.1% by weight of the total weight of the composition.

As a rule, component (g3), if present, amounts to from 2 to 30% by weight, preferably up to 25% by weight and in particular up to 20% by weight, of the total weight of the composition.

Besides water, the compositions may encompass further solvents of soluble constituents or diluents of insoluble constituents of the composition.

Substances which can be used in principle are, for example, mineral oils, synthetic oils and vegetable and animal oils, and also low-molecular-weight hydrophilic solvents such as alcohols, ethers, ketones and the like.

Substances which must therefore be mentioned are, on the one hand, aprotic or apolar solvents or diluents, such as mineral oil fractions of medium to high boiling point, for example kerosene and diesel oil, furthermore coal tar oils, hydrocarbons, liquid paraffins, for example $C_8$-to $C_{30}$-hydrocarbons of the n- or iso-alkane series or mixtures of these, optionally hydrogenated or partially hydrogenated aromatics or alkylaromatics from the benzene or naphthalene series, for example aromatic or cycloaliphatic $C_7$- to $C_{18}$-hydrocarbon compounds, aliphatic or aromatic carboxylic acid or dicarboxylic acid esters, fats or oils of vegetable or animal origin, such as mono-, di- and triglycerides, in pure form or as a mixture, for example in the form of oily extracts of natural materials, for example olive oil, soya oil, sunflower oil, castor oil, sesame seed oil, corn oil, peanut oil, rapeseed oil, linseed oil, almond oil, castor oil, safflower oil, their raffinates, for example hydrogenated or partially hydrogenated products thereof, and/or their esters, in particular the methyl and ethyl esters.

Examples of $C_8$- to $C_{30}$-hydrocarbons of the n- or iso-alkane series are n- and iso-octane, -decane, -hexadecane, -octadecane, -eicosane, and preferably hydrocarbon mixtures such as liquid paraffin (which, in technical-grade quality, may comprise up to approximately 5% of aromatics) and a $C_{18}$–$C_{24}$-mixture which is commercially available from Texaco under the name Spraytex oil.

The aromatic or cycloaliphatic $C_7$–$C_{18}$ hydrocarbon compounds include, in particular, aromatic or cycloaliphatic solvents from the alkylaromatics series. These compounds can be unhydrogenated, partially hydrogenated or fully hydrogenated. Such solvents include, in particular, mono-, di- or trialkylbenzenes, mono-, di- or trialkyl-substituted tetralins and/or mono-, di-, tri- or tetraalkyl-substituted naphthalenes (alkyl is preferably $C_1$–$C_6$-alkyl). Examples of such solvents are toluene, o-, m-, p-xylene, ethylbenzene, isopropylbenzene, tert-butylbenzene and mixtures, such as the Exxon products sold under the name Shellsol and Solvesso, for example Solvesso 100, 150 and 200.

Examples of suitable monocarboxylic esters are oleic esters, in particular methyl oleate and ethyl oleate, lauric esters, in particular 2-ethylhexyl laurate, octyl laurate and isopropyl laurate, isopropyl myristate, palmitic esters, in particular 2-ethylhexyl palmitate and isopropyl palmitate, stearic esters, in particular n-butyl stearate and 2-ethylhexyl 2-ethylhexanoate.

Examples of suitable dicarboxylic esters are adipic esters, in particular dimethyl adipate, di-n-butyl adipate, di-n-octyl adipate, di-iso-octyl adipate, also termed bis(2-ethylhexyl) adipate, di-n-nonyl adidipate, di-iso-nonyl adidipate and ditridecyl adipate; succinic esters, in particular di-n-octyl succinate and di-iso-octyl succinate, and di(iso-nonyl) cyclohexane 1,2-dicarboxylate.

As a rule, the above-described aprotic solvents or diluents amount to less than 30% by weight, preferably less than 20% by weight and in particular less than 5% by weight, of the total weight of the composition.

Some of these aprotic solvents or diluents have adjuvant, i.e. in particular activity-enhancing, properties. This applies in particular to said mono- and dicarboxylic acids. Under this aspect, such adjuvants, forming a further formulation (stand-alone product), can be mixed with the compositions according to the invention at an expedient point in time, as a rule shortly before application.

On the other hand, protic, or polar, solvents or diluents must be mentioned, for example $C_2$–$C_8$-monoalcohols such as ethanol, propanol, isopropanol, butanol, isobutanol, tert-butanol, cyclohexanol and 2-ethylhexanol, $C_{3–C8}$-ketones such as diethyl ketone, t-butyl methyl ketone and cyclohexanone, and aprotic amines such as N-methyl- and N-octylpyrrolidone.

As a rule, the above-described protic, or polar, solvents or diluents amount to less than 30% by weight, preferably less than 20% by weight and in particular less than 15% by weight, of the total weight of the composition.

Sedimentation inhibitors may also be used, in particular for suspension concentrates. These serve especially for the rheological stabilization. Products which may be mentioned in particular in this case are mineral products, for example bentonites, talcites and hectorites.

Further additives which may be useful can be found, for example, among mineral salt solutions which are employed for alleviating nutritional and trace element deficiencies, nonphytotoxic oils and oil concentrates, antidrift reagents, antifoams, in particular those of the silicone type, for example Silicon SL, which is available from Wacker, and the like.

In accordance with a particular embodiment, the present invention relates to suspension concentrates comprising
 (a) 10 to 70% by weight of at least one active ingredient selected from among (a1) N,N,N-trimethyl-N-β-chloroethylammonium chloride, of the formula (Ia) and (a2) N,N-dimethylpiperidinium chloride, of the formula (Ib);
 (b) 10 to 60% by weight of water;
 (c) 5 to 50% by weight of at least one optionally end-capped ethylene oxide/propylene oxide block copolymer of the formula (IVa);
 (d) 5 to 40% by weight of ammonium nitrate;
 (e1) 0.5 to 30% by weight of prohexadione-calcium, of the formula (IIa).

This embodient can advantageously optionally comprise one or more of the components mentioned below:
 (f1) 0.5 to 30% by weight of at least one nonionic surfactant of the formula (V), in particular a sorbitol polyethoxy fatty acid ester;
 (g1) 0.1 to 7.5% by weight of at least one calcium salt.

Compositions according to the invention can be prepared in a manner known per se. To this end, at least some of the components are combined. In this context, it must be noted that products, in particular commercially available products, can be used whose constituents may contribute to different components. For example, a particular surfactant may be dissolved in an aprotic solvent, so that this product can contribute to various components. Furthermore, small amounts of undesired substances may be introduced together with commercially available products. For example, the products to be processed to give the compositions according to the invention are advantageously selected under the aspect of as low as possible a content of anions which can form sparingly soluble salts with the cations present in the compositions, for example the ammonium and in particular the calcium ions. As a mixture, the products which have been combined are then generally to be mixed intensively with each other to give a homogeneous mixture and, if required, ground, for example in the case of suspensions.

Mixing can be effected in a manner known per se, for example by homogenizing using suitable devices such as KPG stirrers or magnetic stirrers.

Grinding too is a procedure which is known per se. The milling elements which can be used are glass milling elements or other mineral or metal milling elements, as a rule with a size of 0.1–30 mm and in particular 0.6–2 mm. As a rule, the mixture is comminuted until the desired particle size has been achieved.

In general, grinding can be effected as a circulating operation, i.e. the SC is circulated by pumping, or as a passage operation, i.e. an SC batch is completely and repeatedly pumped or run through the mill.

Grinding can be effected with conventional ball mills, bead mills or stirrer mills, for example in a Dyno mill (Bachofen), with batch sizes of, for example, 0.5 up to 1 liter in what is known as a passage operation. After several—in particular 4 to 6—passages (pumping the suspension through the mill with the aid of a roller pump), mean particles sizes of from 0.5 to 10 $\mu$m are achieved, according to evaluation under the microscope.

In accordance with a particular embodiment, the present invention relates to a process for the preparation of a composition by combining the components, wherein a mixture of ammonium nitrate and calcium carbonate is used. This procedure not only has the advantage that conventional and/or commercially available fertilizer granules can be used, but also that it simultaneously contributes to component (g1). Ammonium nitrate- and calcium-carbonate-comprising mixtures, in particular fertilizer mixtures, which are advantageously used are those in which the calcium carbonate amounts to from 0.5 to 7.5% by weight, preferably from 1 to 5% by weight and in particular from 2 to 4% by weight of the total weight of the mixture. Preferably, at least some of the calcium carbonate is then reacted with acid when the process is carried out. This results in the corresponding calcium salt, which contributes to component (g1). It is expedient to use the acid in a slightly substoichiometric amount or else in an equimolar amount based on calcium carbonate, for example approximately 0.8 to 1 molar equivalent.

The present invention also relates to the use of compositions according to the invention as bioregulators for a series of various possible uses, for example in plant production, agriculture and horticulture.

For example, bioregulatory active ingredients can affect plant growth (growth regulators). Virtually all development stages of a plant can be detected.

Thus, for example, the vegetative growth of the plants can be inhibited greatly, which manifests itself in particular in a reduced longitudinal growth. Accordingly, the treated plants exhibit stunted growth; moreover, the leaf color is darker. A reduced intensity of the growth of grasses on verges, hedgerows, waterway embankments and on lawns such as parks, sportsgrounds and orchards, ornamental lawns and airfields, so that laborious and expensive grass cutting can be reduced is advantageous in practice.

Also of economic interest is an improved standing ability of crops which are susceptible to lodging, such as cereals, maize and sunflowers. The shortening and strengthening of the stem which are caused in this process reduce or eliminate the danger of "lodging" (bending over) of plants under unfavorable weather conditions before the harvest. Also of importance is the use of growth regulators for inhibiting the longitudinal growth and for modifying the maturation process over time in cotton. This makes possible the completely mechanical harvesting of this crop plant. In fruit trees and other trees, pruning costs can be saved by using the growth regulators. Moreover, biennial bearing of fruit trees can be avoided by using growth regulators. By using growth regulators, it is also possible to increase or inhibit lateral branching of the plants. This is of interest when the formation of lateral shoots (suckers) is to be inhibited in favor of foliar growth, for example in the case of tobacco plants.

Using growth regulators, it is also possible considerably to increase frost resistance, for example in the case of winter oilseed rape. Here, firstly, longitudinal growth and the development of too lush foliage or plant biomass (which is therefore particularly sensitive to frost) are inhibited. On the other hand, the young oilseed rape plants are retained in the vegetative development after sowing and before the winter frosts arrive, despite favorable growth conditions. Thus, the risk of frost damage of those plants which tend to prematurely overcome floral inhibition and enter the generative phase is also eliminated. In other crops too, for example in winter cereals, it is advantageous when tillering of the stands is good in fall owing to treatment with growth regulators, while the stands are not too lush at the onset of winter. In this manner, increased sensitivity to frost and—owing to the relatively low foliage or plant biomass—attack by various diseases (for example fungal diseases) can be prevented. Moreover, the inhibition of vegetative growth makes possible in many crop plants greater plant density on the soil, so that higher yields can be achieved relative to the soil area.

With the aid of growth regulators, increased yields of plant parts and also plant constituents can be achieved. Thus, for example, it is also possible to induce the growth of larger amounts of buds, flowers, leaves, fruits, seed kernels, roots and tubers, to increase the sugar content in sugarbeet, sugar cane and citrus fruit, to increase the protein content in cereals or soybeans or to stimulate rubber trees to obtain an increased latex flow. In this context, the active ingredients can lead to increased yields by engaging in the plant metabolism or by promoting or inhibiting the vegetative and/or generative growth. Finally, not only shortened or extended development stages, but also accelerated or delayed maturity of the harvested plant parts pre- or post-harvest can be achieved by using plant growth regulators.

Of economic interest is, for example, facilitated harvesting which is made possible by a dehiscence which is concentrated over time, or by reduced adherence to the tree, in the case of citrus fruit, olives or other species and varieties of pome fruit, stone fruit and hard-shelled fruit. The same mechanism, that is to say the promotion of the formation of abscission tissue between fruit and leaf or shoot part of the plant is also essential for the readily-controlled defoliation of useful plants such as, for example, cotton.

Moreover, the water consumption of plants can be reduced by using growth regulators. This is particularly important for agricultural areas which must be irrigated artificially, which is very costly, for example in arid or semiarid regions. By using growth regulators, the irrigation intensity can be reduced and the economy of the management improved. Under the effect of growth regulators, utilization of the existing water is better since, inter alia, the degree of opening of the stomata is reduced, a thicker epidermis and cuticula are formed, root penetration into the soil is improved, the transpiring leaf area is reduced, or the microclimate in the crop plant stand is affected favorably by a more compact growth.

Compositions according to the invention are used in particular as bioregulators in cereal production and especially for wheat, barley, oats and rye or else maize and rice.

To this end, the compositions according to the invention are converted in the customary manner prior to use as a rule by dilution into a form which is suitable for application. Preferred is dilution with water or else aprotic solvents, for example by the tank mix method. The use in the form of a spray mixture is preferred. As a rule, the application is effected pre-emergence or post-emergence.

For a customary tank mix spray mixture, from 0.2 to 5.0, preferably from 0.3 to 3.0 and in particular from 0.35 to 2.0 l of the composition according to the invention are diluted with water to 50 to 2 000 l and in particular 100 to 1 000 l (per hectare). If appropriate, from 0.1% by weight to 5% by weight (based on the spray mixture) of further anionic, cationic or nonionic surfactants, auxiliaries, polymers and/or the abovementioned other herbicidal active ingredients are added to the tank mix spray mixture. Examples of substances for such surfactants and further auxiliaries have already been described above. Substances which must be mentioned in particular are starch and starch derivatives, for example a carboxyl- and sulfo-containing starch (Nu-Film by Union Carbide Corp.) and spreading agents and extenders, such as Vapor Guard by Miller Chemical & Fertilizer Corp.

For the purposes of the present invention, terms such as alkyl, alkoxy and the like encompass straight-chain or branched hydrocarbon groups such as methyl, ethyl, n-propyl, i-propyl, n-butyl, i-butyl, sec-butyl, t-butyl, n-pentyl, n-hexyl, n-octyl, 2-ethylhexyl, n-nonyl, iso-nonyl, n-decyl, iso-decyl, n-undecyl, iso-undecyl, n-dodecyl, iso-dodecyl, n-tridecyl, iso-tridecyl, stearyl, n-eicosyl, preferably having—unless otherwise defined—1 to 8, in particular 1 to 6 and especially preferably 1 to 4 carbon atoms in the case of short-chain radicals and 6 to 30, in particular 8 to 24 and especially preferably 12 to 24 carbon atoms in the case of long-chain radicals.

The term "cycloalkyl" encompasses mono- or bicyclic saturated hydrocarbon groups which are optionally mono-, di- or trisubstituted by $C_1$–$C_4$-alkyl, such as cyclopropyl, cyclobutyl, cyclopentyl and especially cyclohexyl and the like, preferably having—unless otherwise indicated—3 to 10, in particular 3 to 6 and especially preferably 6 carbon atoms. What has been said above applies analogously to "cycloalkylene" as corresponding divalent radicals, of which the cycloalk-1-ylenes are preferred.

The term "alkenyl" encompasses straight-chain or branched unsaturated hydrocarbon groups which preferably have one, two or three double bonds, such as ethenyl, prop-2-en-1-yl, oleyl and the like, preferably having—unless otherwise indicated—3 to 8, in particular 2 to 6 and especially preferably 2 to 4 carbon atoms in the case of short-chain radicals and 6 to 30, in particular 8 to 24 and especially preferably 12 to 24 carbon atoms in the case of long-chain radicals.

The term "alkylene" encompasses straight-chain or branched divalent radicals such as methylene, eth-1,1-ylene, eth-1,2-ylene, prop-1,1-ylene, prop-1,2-ylene, prop-1,3-ylene, prop-2,2-ylene, but-1,1-ylene, but-1,2-ylene, but-1,3-ylene, but-1,4-ylene, but-2,4-ylene, 2-methylprop-1,3-ylene, pent-1,1-ylene, pent-1,2-ylene, pent-1,3-ylene, pent-1,4-ylene, pent-1,5-ylene, pent-2,2-ylene, pent-2,3-ylene, pent-2,4-ylene, pent-3,3-ylene, 1-methylbut-1,4-ylene, 2-methylbut-1,4-ylene, and the like, preferably having—unless otherwise indicated—2 to 18, in particular 2 to 10 and especially preferably 2 to 6 carbon atoms.

The term "halogen" preferably represents fluorine, chlorine, bromine and iodine, in particular fluorine and especially chlorine.

The invention is illustrated in greater detail by the examples which follow:

PREPARATION EXAMPLES

Reference Example 1

SL Formulations

The SL formulations described in the examples are prepared by stirring the various components together, using a magnetic stirrer. The active ingredient chlormequat chloride, abbreviated hereinbelow to CCC for chlorocholine chloride, was employed as aqueous active ingredient concentrate with 750 g/l CCC. Mepiquat chloride, abbreviated to MQC hereinbelow, is employed as aqueous active ingredient concentrate with 610 g/l MQC.

Reference Example 2

SC Formulations

To prepare the SC formulations described in the examples, the active ingredient concentrates are treated with suitable amounts of ammonium nitrate and 50 g of water. The ammonium nitrate is dissolved with stirring. The other components stated in each case are subsequently added, prohexadione-calcium is stirred in until the active ingredient has reached 50 g/l, and the mixture is made up to 1 l with water (approx. 50 ml).

The mixture is then subjected to five grinding passages in a 0.5 l benchtop Dyno mill using 1 mm glass beads, at a precooling setting of 15° C. and at most 25° C. at the product discharge point (roller pump at 5 l/h), until approximately 80% of the particles have a size of less than 2 $\mu$m. Finally, the antifoam Silikon SRE is stirred in to give 1.0 g/l.

Examples 1 to 45

SL Formulations

Using the preparation process of reference example 1, SL formulations are prepared as specified in tables 1 and 2 hereinbelow (examples 1 to 45).

TABLE 1

Active ingredients and auxiliaries of specific SL formulations, indicated as ["name"/"parts"], unless otherwise specified

| Ex. | (a) | (b) | (c) | (d) or $NH_4^+X$ |
|---|---|---|---|---|
| 1 | CCC/3.5 | PE 6400/1.5 | 1.82 (26.7%) | — |
| 2 | CCC/3.5 | PE 6400/1.5 | 2.32 (31.7%) | — |
| 3 | CCC/3.5 | PE 6400/1.5 | 2.82 (36.1%) | — |
| 4 | CCC/3.5 | PE 6400/1.5 | 3.32 (39.1%) | — |
| 5 | CCC/3.5 | PE 6400/1.5 | 3.82 (43.3%) | — |
| 6 | CCC/3.5 | PE 6400/1.5 | 4.22 (45.8%) | — |
| 7 | CCC/3.5 | PE 6400/1.5 | 4.72 (48.6%) | — |

TABLE 1-continued

Active ingredients and auxiliaries of specific SL formulations,
indicated as ["name"/"parts"], unless otherwise specified

| Ex. | (a) | (b) | (c) | (d) or $NH_4^+X$ |
|---|---|---|---|---|
| 8 | CCC/3.5 | PE 6400/1.5 | 1.82 (20.6%) | $NH_4NO_3$/2.0 |
| 9 | CCC/3.5 | PE 6400/1.5 | 2.32 (24.9%) | $NH_4NO_3$/2.0 |
| 10 | CCC/3.5 | PE 6400/1.5 | 2.82 (28.7%) | $NH_4NO_3$/2.0 |
| 11 | CCC/3.5 | PE 6400/1.5 | 3.32 (32.2%) | $NH_4NO_3$/2.0 |
| 12 | CCC/3.5 | PE 6400/1.5 | 3.82 (35.3%) | $NH_4NO_3$/2.0 |
| 13 | CCC/3.5 | PE 6400/1.5 | 4.22 (37.6%) | $NH_4NO_3$/2.0 |
| 14 | CCC/3.5 | PE 6400/1.5 | 4.72 (40.3%) | $NH_4NO_3$/2.0 |
| 15 | CCC/2 | PE 6400/1.5 | 4.2 | $NH_4NO_3$/2.0 |
| 16 | CCC/2 | PE 6400/1.5 | 4.2 | $NH_4HCOO$/2.0 |
| 17 | CCC/2 | PE 6400/1.5 | 4.2 | $NH_4Cl$/2.0 |
| 18 | CCC/2 | PE 6400/1.5 | 4.2 | $(NH_4)_2SO_4$/2.0 |
| 19 | CCC/2 | PE 6400/1.5 | 4.2 | $(NH_4)_3PO_4$/2.0 |
| 20 | CCC/2 | PE 6400/1.5 | 4.2 | $(NH_4)_3$ citrate/2.0 |
| 21 | CCC/2 | PE 6400/1.5 | 4.2 | $NH_4CH_3COO$/2.0 |
| 22 | CCC/2 | PE 6800/1.5 | 4.2 | $NH_4NO_3$/2.0 |
| 23 | CCC/2 | PE 6800/1.5 | 4.2 | $NH_4HCOO$/2.0 |
| 24 | CCC/2 | PE 6800/1.5 | 4.2 | $NH_4Cl$/2.0 |
| 25 | CCC/2 | PE 6800/1.5 | 4.2 | $(NH_4)_2SO_4$/2.0 |
| 26 | CCC/2 | PE 6800/1.5 | 4.2 | $(NH_4)_3PO_4$/2.0 |
| 27 | CCC/2 | PE 6800/1.5 | 4.2 | $(NH_4)_3$ citrate/2.0 |
| 28 | CCC/2 | PE 6800/1.5 | 4.2 | $NH_4CH_3COO$/2.0 |
| 29 | CCC/2 | PE 10500/1.5 | 4.2 | $NH_4NO_3$/2.0 |
| 30 | CCC/2 | PE 10500/1.5 | 4.2 | $(NH_4)_3PO_4$/2.0 |
| 31 | CCC/2 | PE 10500/1.5 | 4.2 | $(NH_4)_3$ citrate/2.0 |

Examples 1 to 7 show that the mixtures, which are 2-phase at lower water contents, undergo transition into 1-phase mixtures only from a relatively high water content of 45% and above. However, even these 1-phase mixtures are turbid and undergo transition into 2-phase systems upon prolonged storage.

If ammonium nitrate is added, the corresponding examples 8 to 14 show that 1-phase homogeneous systems are already obtained when the water contents are substantially lower. While the precipitation of ammonium chloride is still observed in accordance with examples 8 and 9 and the systems are high-viscous or pasty, viscous systems or systems with low viscosity are obtained in examples 10 to 14 with increasing water content. For example, the viscosities of examples 10 to 12 are approximately 680, 168 and 45 mPas, respectively.

In contrast, examples 16 to 21, 23 to 28, 30 and 31 show that 2-phase systems are obtained with ammonium salts other than ammonium nitrate, while the addition of ammonium nitrate in accordance with examples 15, 22 and 29 leads to 1-phase and in particular flowable systems under otherwise identical conditions.

Without the addition of ammonium nitrate, 1-phase systems cannot be achieved even when further surface-active compounds, for example the (glycerol) fatty acid ethoxylates, alkylglycosides or polyethoxylated sorbitol poly-fatty acid esters used in examples 32 to 38 hereinbelow, are employed jointly with the EO/PO block copolymers according to the invention. By addition of ammonium nitrate, however, precisely these mixtures can be converted into 1-phase systems (cf. examples 39 to 45).

TABLE 2

Active ingredients and auxiliaries of specific SL formulations,
indicated as ["name"/"parts"], unless otherwise specified

| Ex. | (a) | (b) | (c) | (d) | (f) |
|---|---|---|---|---|---|
| 32 | MQC/5.12 | PE 6400/1.0 | 1.1 | — | WO-CE/0.5 |
|  |  |  |  |  | AG 6202/0.5 |
|  |  |  |  |  | G 1086/0.5 |
| 33 | MQC/5.12 | PE 6400/1.0 | 1.0 | — | WO-CE/0.5 |
|  |  |  |  |  | AG 6202/0.5 |
|  |  |  |  |  | G 1086/0.5 |
| 34 | MQC/5.12 | PE 6400/1.5 | 1.35 | — | G 1086/0.75 |
| 35 | MQC/5.12 | PE 6400/1.5 | 1.25 | — | G 1086/0.75 |
| 36 | MQC/5.12 | PE 6400/1.5 | 1.25 | — | G 1049/0.75 |
| 37 | MQC/5.12 | PE 6400/1.5 | 0.76 | — | ELP/0.75 |
|  |  |  |  |  | AG 6202/0.5 |
| 38 | MQC/5.12 | PE 6400/1.5 | 1.25 | — | HE/0.75 |
| 39 | MQC/5.12 | PE 6400/1.0 | 1.1 | $NH_4NO_3$/2.0 | WO-CE/0.5 |
|  |  |  |  |  | AG 6202/0.5 |
|  |  |  |  |  | G 1086/0.5 |
| 40 | MQC/5.12 | PE 6400/1.0 | 1.0 | $NH_4NO_3$/2.0 | WO-CE/0.5 |
|  |  |  |  |  | AG 6202/0.5 |
|  |  |  |  |  | G 1086/0.5 |
| 41 | MQC/5.12 | PE 6400/1.5 | 1.35 | $NH_4NO_3$/2.0 | G 1086/0.75 |
| 42 | MQC/5.12 | PE 6400/1.5 | 1.25 | $NH_4NO_3$/2.0 | G 1086/0.75 |
| 43 | MQC/5.12 | PE 6400/1.5 | 1.25 | $NH_4NO_3$/2.0 | G 1049/0.75 |
| 44 | MQC/5.12 | PE 6400/1.5 | 0.76 | $NH_4NO_3$/2.0 | ELP/0.75 |
|  |  |  |  |  | AG 6202/0.5 |
| 45 | MQC/5.12 | PE 6400/1.5 | 1.25 | $NH_4NO_3$/2.0 | HE/0.75 |

Examples 46 to 52

SC Formulations

Using the preparation process in accordance with reference example 2, SC formulations are prepared as stated in table 3 which follows (examples 46 to 52).

TABLE 3

Active ingredients and auxiliaries of specific SC formulations,
stated as ["name" ("g/l")], unless otherwise specified

| Ex. | (a) | (b) | (c) | (d) | (e) | (f) | (g) |
|---|---|---|---|---|---|---|---|
| 46 | MQC (300) | PE 6400 (100) | ad 11 | $NH_4NO_3$ (200) | PC (50) | WO-CE (50) AG 6202 (50) G 1086 (50) | — |
| 47 | MQC (300) | PE 6400 (100) | ad 11 | $NH_4NO_3$ (200) | PC (50) | WO-CE (50) AG 6202 (50) G 1086 (50) | $CaCl_2$ (10) |
| 48 | MQC (300) | PE 6400 (150) | ad 11 | $NH_4NO_3$ (200) | PC (50) | G 1086 (75) | |
| 49 | MQC (300) | PE 6400 (150) | ad 11 | $NH_4NO_3$ (200) | PC (50) | G 1086 (75) | $CaCl_2$ (10) |
| 50 | MQC (300) | PE 6400 (150) | ad 11 | $NH_4NO_3$ (200) | PC (50) | G 1049 (75) | $CaCl_2$ (10) |
| 51 | MQC (300) | PE 6400 (150) | ad 11 | $NH_4NO_3$ (200) | PC (50) | ELP (75) AG 6202 (50) | $CaCl_2$ (10) |
| 52 | MQC (300) | PE 6400 (150) | ad 11 | $NH_4NO_3$ (200) | PC (50) | HE (75) | $CaCl_2$ (10) |

Physical Properties: Stability

The stability of suspension concentrates (examples 46 to 52) is assessed in a rapid-storage test. To this end, the samples are stored for 14 days in sealed glass containers at 54° C. The active ingredient concentration is subsequently determined. This value in relation to the original active ingredient content is a measure for the stability of the suspension concentrate.

TABLE 5

Stability of SC formulations

| Ex. | Residual active ingredient content in % based on starting quantity | |
|---|---|---|
|  | MQC | PC |
| 46 | 99.2 | 96.7 |
| 47 | 100 | 97.5 |
| 48 | 100 | 96.9 |
| 49 | 98.4 | 98.2 |
| 50 | 99.4 | 100 |
| 51 | 98.9 | 97.2 |
| 52 | 100 | 96.5 |

The SC formulations described in examples 46 to 52, which are based on a homogeneous phase, were unobjectionable and homogeneous in physical and emulsion terms before and after storage for 14 days at 54° C. The storage stability, which was assessed on the basis of the decomposition of the two active ingredients, was satisfactory in all cases with a residual active ingredient content of not less than 95%. The addition of calcium chloride resulted in an additional stabilization of prohexadione-calcium.

The active ingredients and auxiliaries used in the above examples are illustrated in table 4 which follows.

TABLE 4

| Name (abbreviation) | Structural type/feedstock | Manufacturer |
|---|---|---|
| Component (a) | | |
| CCC | Chlorocholine chloride, chlormequat chloride | BASF AG |
| MQC | Mepiquat chloride | BASF AG |
| PC | Prohexadione-calcium | BASF AG/ Kumiai |
| Component (b) | | |
| Pluronic PE 6400 | EO/PO block copolymer; 40% by weight of EO; 2900 | BASF |
| Pluronic PE 6800 | EO/PO block copolymer; 80% by weight of EO; 8000 | BASF |
| Pluronic PE 10500 | EO/PO block copolymer; 50% by weight of EO; 6500 | BASF |
| Component (f) | | |
| Cremophor WO-CE 5115 | Oleyl glycerol ether ethoxylate; CAS-No. 104376-61-6 | BASF |
| Emulan ELP | Castor oil x 11 EO | BASF |
| AG 6202 | 2-Ethylhexyl glucoside | Witco |
| Atlas G 1086 | Polyoxyethylene sorbitol hexaoleate | Uniqema |
| Atlas G 1049 | Polyoxyethylene sorbitol heptaisostearate | Uniqema |
| Glycerox HE | Coconut fatty acid ester of ethoxylated glyercol; CAS-No. 68553-03-7 | Croda |

We claim:

1. A composition based on a homogeneous phase, comprising (a) at least one active ingredient of the formula (I)

$$\begin{array}{c} R^1 \quad R^2 \\ \diagdown \stackrel{+}{N} \diagup \\ H_3C \diagup \quad \diagdown CH_3 \end{array} \quad X^-$$ (I)

where $R^1$, $R^2$ and X have the following meanings:
$R^1$ is $C_1$–$C_4$-alkyl;
$R^2$ is $C_1$–$C_4$-alkyl, cyclopentenyl, halo-$C_1$–$C_6$-alkyl; or $R^1$ and $R^2$ together are a radical —$(CH_2)_5$—, —$(CH_2)_2$—O—$(CH_2)_2$— or —$(CH_2)$—CH=CH—$(CH_2)$—NH—;
x is an anionic group;

(b) water;

(c) at least one optionally end-capped ethylene oxide/ propylene oxide block copolymer;

(d) ammonium nitrate.

2. A composition as claimed in claim 1, wherein the homogeneous phase has a density of at least 1.04 g/l, preferably of at least 1.07 g/l.

3. A composition as claimed in claim 1, wherein the active ingredient of the formula I is selected from among (a1) N,N,N-trimethyl-N-β-chloroethylammonium chloride, of the formula (Ia), $$\begin{array}{c} CH_3 \\ | \\ H_3C — \stackrel{+}{N} — \diagdown Cl \quad Cl^- \\ | \\ CH_3 \end{array}$$ (Ia)

(a2) N,N-dimethylpiperidinium chloride, of the formula (Ib), (Ib)

and (a3) N,N-dimethylmorpholinium chloride, of the formula (Ic)

(Ic)

4. A composition as claimed in claim 1, wherein the optionally end-capped ethylene oxide/propylene oxide block copolymer is selected from among polymers of the formula (IVa)

$$R^{16}O—(C_2H_4O)_p—(C_3H_6O)_q—(C_2H_4O)_r—R^{17}$$ (IVa)

or polymers of the formula (IVb)

$$R^{16}O—(C_3H_6O)_p—(C_2H_4O)_q—(C_3H_6O)_r—R^{17}$$ (IVb)

where p, q, r independently of one another correspond to a value in the range of from 3 to 250, and $R^{16}$, $R^{17}$ independently of one another are hydrogen, $C_1$–$C_4$-alkyl and $C_1$–$C_4$-alkyl-CO.

5. A composition as claimed in claim 1, comprising (e) at least one further bioregulator.

6. A composition as claimed in claim 5, comprising (e1) at least one active ingredient of the formula (II)

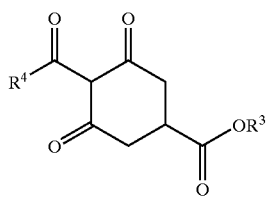

where $R^3$ and $R^4$ have the following meanings:

$R^3$ is hydrogen, $C_1$–$C_4$-alkyl, $C_1$–$C_4$-alkyl-S—$C_1$–$C_4$-alkyl, phenyl, substituted phenyl;

R4 is $C_1$–$C_4$-alkyl, $C_3$–$C_6$-cycloalkyl, benzyl, substituted benzyl, phenethyl, phenoxymethyl, 2-thienylmethyl, $C_1$–$C_4$-alkoxymethyl, $C_1$–$C_4$-alkylthiomethyl;

or an agriculturally useful salt thereof.

7. A composition as claimed in claim 6, wherein the radical $R^4$ represents ethyl and the radical $R^3$ represents hydrogen, $C_1$–$C_4$-alkyl or an agriculturally useful cation.

8. A composition as claimed in claim 7, wherein the active ingredient of the formula II is prohexadione-calcium, of the formula (IIa)

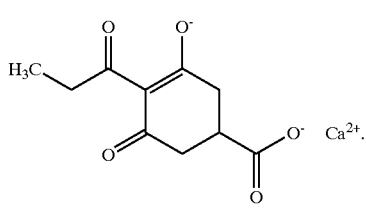

9. A composition as claimed in claim 5, comprising (e2) at least one active ingredient of the formula (IIIa)

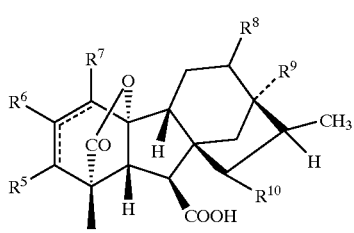

where the radicals $R^5$, $R^6$, $R^7$, $R^8$, $R^9$ and $R^{10}$ independently of one another are hydrogen or hydroxyl and the broken line denotes an optional double bond either between the carbon atoms in positions 1 and 2 or between the carbon atoms in positions 2 and 3;

and/or at least one active ingredient of the formula

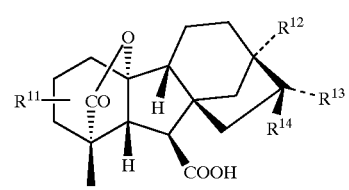

where $R^{11}$ indicates that ring A (i) has no further functionality, or (ii) has a 1,2-double bond or a 2,3-double bond or (iii) has OH, F, $C^1$ or Br in position 3α or 3β, it being possible for a 1,2-double bond to be present or not, or (iv) has OH, F, Cl or Br in position 3α or 3β, it being possible for a 2,3-double bond to be present or not;

$R^{12}$ is H or OH, OC(=O)$R^{15}$ or OR$^{15}$;

$R^{13}$, $R^{14}$ independently of one another are H, F, Cl, Br, $C_1$–$C_6$-alkyl, $C_2$–$C_6$-alkenyl, $C_3$–$C_6$-cycloalkyl or $CH_2X$, where X is F, Cl or Br;

$R^{15}$ is $C_1$–$C_6$-alkyl.

10. A composition as claimed in claim 9, wherein the active ingredient of the formula (IIIb) is exo-16,17-dihydro-GA5-13-acetate, of the formula (IIIc)

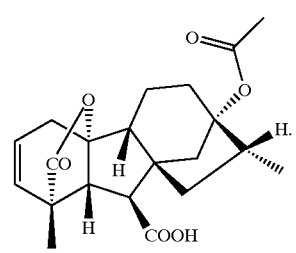

11. A composition as claimed claim 1, comprising (f) at least one further surfactant.

12. A composition as claimed in claim 11, wherein the surfactant is selected from among (f1) non ionic surfactants of the formula (V),

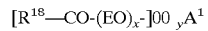

$$[R^{18}—CO-(EO)_x-]00\ _yA^1 \qquad (V)$$

where $R^{18}$ is a straight-chain or branched, saturated or unsaturated, unhydroxylated, monohydroxylated or dihydroxylated aliphatic radical having 8 to 30 carbon atoms, the total of all x is zero to 100, y is 1 to 7, $A^1$ is hydroxyl or $C_1$–$C_4$-alkoxy if y is 1 or $A^1$ is derived from a $C_3$–$C_7$-polyol if y is 2 to 7.

13. A composition as claimed in claim 12, wherein component (f1) is selected from among castor oil polyethoxylates, sorbitol polyethoxyoleates, sorbitol polyethoxyisostearates and mixtures of these.

14. A composition as claimed in claim 1, comprising (g) at least one further auxiliary selected from among
 (g1) calcium salts
 (g2) chelating agents
 (g3) urea
 (g4) further solvents or diluents.

15. A composition as claimed in claim 1, comprising (a) 10 to 70% by weight of at least one active ingredient of formulae (Ia) and/or (Ib)
 (a1) N,N,N-trimethyl-N-B-chloroethylammonium chloride, of the formula (Ia),

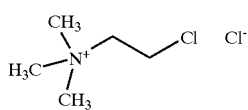
(Ia)

(a2) N,N-dimethylpiperidinium chloride, of the formula (Ib),

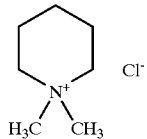
(Ib)

(b) 10 to 60% by weight of water;
(c) 5 to 50% by weight of at least one optionally end-capped ethylene oxide/propylene oxide block copolymer of the formula (IVa):

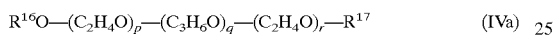
(IVa)

where
p, q, r independently of one another correspond to a value in the range of from 3 to 250, and $R^{16}$, $R^{17}$ independently of one another are hydrogen, $C_1$–$C_4$-alkyl and $C_1$–$C_4$-alkyl-CO;
(d) 5 to 40% by weight of ammonium nitrate; and
(e1) 0.5 to 30% by weight of an active ingredient of the formula (IIa)

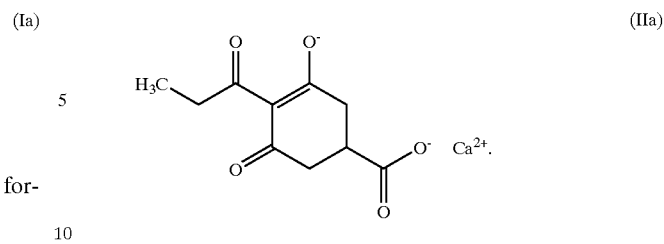
(IIa)

16. A process for the preparation of the composition as claimed in claim 1 by extensively mixing the components, wherein a mixture of ammonium nitrate and calcium carbonate is used.

17. A process as claimed in claim 16, wherein fertilizer granules are used.

18. A process as claimed in claim 16, wherein at least some of the calcium carbonate is reacted with acid.

19. A method for homogenizing a mixture comprising
(a) at least one active ingredient of the formula (I)

(I)

where $R^1$, $R^2$ and X are as defined in claim 1;
(b) water;
(c) at least one optionally end-capped ethylene oxide/propylene oxide block copolymer,
which process comprises adding ammonium nitrate to said mixture.

20. A method for bioregulation in plant production, in agriculture or in horticulture, which comprises treating a plant with a composition as claimed in claim 1.

* * * * *

UNITED STATES PATENT AND TRADEMARK OFFICE
CERTIFICATE OF CORRECTION

PATENT NO. : 6,878,673 B2
DATED : April 12, 2005
INVENTOR(S) : Kober et al.

It is certified that error appears in the above-identified patent and that said Letters Patent is hereby corrected as shown below:

Column 24,
Line 14, delete "double bond or (iii) has OH, F, $C^1$ or Br in position 3α" and substitute -- double bond or (iii) has OH, F, Cl or Br in position 3α --.

Signed and Sealed this

Twenty-third Day of May, 2006

JON W. DUDAS
*Director of the United States Patent and Trademark Office*